United States Patent
Pryor (10) Patent No.: US 8,968,379 B2
(45) Date of Patent: Mar. 3, 2015

(54) STENT DELIVERY SYSTEM WITH MULTIPLE EVENLY SPACED PULLWIRES

(75) Inventor: Jack Pryor, San Diego, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2067 days.

(21) Appl. No.: 11/218,919

(22) Filed: Sep. 2, 2005

(65) Prior Publication Data

US 2007/0055340 A1   Mar. 8, 2007

(51) Int. Cl.
| | | |
|---|---|---|
| A61F 2/06 | (2013.01) | |
| A61F 2/95 | (2013.01) | |
| A61M 25/01 | (2006.01) | |
| A61F 2/966 | (2013.01) | |
| A61M 25/00 | (2006.01) | |

(52) U.S. Cl.
CPC .......... *A61F 2/95* (2013.01); *A61F 2002/9517* (2013.01); *A61F 2002/9665* (2013.01); *A61M 25/0136* (2013.01); *A61M 25/0147* (2013.01); *A61M 2025/0037* (2013.01); *A61M 2025/004* (2013.01)
USPC ......................................................... 623/1.11

(58) Field of Classification Search
USPC .............. 623/1.2, 1.23, 1.11–1.13, 1.21, 1.27
See application file for complete search history.

(56) References Cited

U.S. PATENT DOCUMENTS

| | | | | |
|---|---|---|---|---|
| 4,996,974 A | * | 3/1991 | Ciarlei ........................... 600/149 |
| 5,195,968 A | * | 3/1993 | Lundquist et al. ......... 604/95.04 |
| 5,346,498 A | * | 9/1994 | Greelis et al. ................. 606/108 |
| 5,358,478 A | * | 10/1994 | Thompson et al. ........ 604/95.04 |
| 5,383,852 A | * | 1/1995 | Stevens-Wright ......... 604/95.04 |
| 5,397,321 A | * | 3/1995 | Houser et al. ................... 606/41 |
| 5,415,664 A | | 5/1995 | Pinchuk |
| 5,462,527 A | * | 10/1995 | Stevens-Wright et al. ... 604/528 |
| 5,501,694 A | * | 3/1996 | Ressemann et al. .......... 606/159 |
| 5,531,686 A | * | 7/1996 | Lundquist et al. ......... 604/95.04 |
| 5,534,007 A | * | 7/1996 | St. Germain et al. ........ 623/1.11 |
| 5,571,135 A | * | 11/1996 | Fraser et al. ................. 623/1.12 |
| 5,611,777 A | * | 3/1997 | Bowden et al. ............ 604/95.01 |
| 5,707,376 A | * | 1/1998 | Kavteladze et al. ......... 623/1.11 |
| 5,715,817 A | * | 2/1998 | Stevens-Wright et al. ... 600/373 |
| 5,891,088 A | * | 4/1999 | Thompson et al. ........ 604/95.04 |
| 5,935,102 A | * | 8/1999 | Bowden et al. ............ 604/95.04 |

(Continued)

FOREIGN PATENT DOCUMENTS

| | | |
|---|---|---|
| EP | 0605796 | 7/1994 |
| WO | WO 97/48343 | 12/1997 |

(Continued)

*Primary Examiner* — Katherine Dowe
*Assistant Examiner* — Erin Colello (57) ABSTRACT

In one aspect, a stent delivery system includes a catheter having two or more pullwire lumens evenly spaced about the central axis of the catheter and thereby balanced within the catheter. Pullwires are positioned in the pullwire lumens. Proximal portions of the pullwires are attached to a connector, which is attached to a master pullwire. The connector has a given range of motion that allows the pullwires to move within the pullwire lumens, thereby ensuring full flexibility of the catheter. The pullwires assume different lengths. A pullwire positioned over the outer curve of a flexed catheter may be longer than a pullwire positioned within the inner curve of the catheter, preventing the catheter from being straightened or displaced by the action of retracting the pullwires. The catheter may serve as either an inner member on which a stent is mounted or a sheath enclosing a stent.

18 Claims, 11 Drawing Sheets

(56) References Cited

U.S. PATENT DOCUMENTS

| | | | |
|---|---|---|---|
| 5,989,280 A * | 11/1999 | Euteneuer et al. | 623/1.1 |
| 6,033,378 A * | 3/2000 | Lundquist et al. | 604/95.01 |
| 6,059,813 A * | 5/2000 | Vrba et al. | 606/198 |
| 6,168,617 B1 * | 1/2001 | Blaeser et al. | 623/1.11 |
| 6,228,110 B1 * | 5/2001 | Munsinger | 623/1.12 |
| 6,231,564 B1 * | 5/2001 | Gambale | 604/528 |
| 6,254,611 B1 * | 7/2001 | Vrba | 606/108 |
| 6,352,561 B1 * | 3/2002 | Leopold et al. | 623/1.23 |
| 6,391,050 B1 * | 5/2002 | Broome | 623/1.11 |
| 6,391,051 B2 * | 5/2002 | Sullivan et al. | 623/1.12 |
| 6,530,897 B2 * | 3/2003 | Nardeo | 604/95.04 |
| 6,537,295 B2 * | 3/2003 | Petersen | 606/200 |
| 6,562,063 B1 * | 5/2003 | Euteneuer et al. | 623/1.12 |
| 6,616,628 B2 * | 9/2003 | Hayzelden | 604/95.04 |
| 6,629,981 B2 * | 10/2003 | Bui et al. | 606/108 |
| 6,676,668 B2 * | 1/2004 | Mercereau et al. | 606/127 |
| 6,702,843 B1 * | 3/2004 | Brown et al. | 623/1.11 |
| 6,702,846 B2 * | 3/2004 | Mikus et al. | 623/1.22 |
| 6,837,886 B2 * | 1/2005 | Collins et al. | 606/41 |
| 6,893,451 B2 * | 5/2005 | Cano et al. | 606/200 |
| 6,939,352 B2 * | 9/2005 | Buzzard et al. | 606/108 |
| 6,997,939 B2 * | 2/2006 | Linder et al. | 606/200 |
| 7,198,636 B2 * | 4/2007 | Cully et al. | 623/1.11 |
| 7,258,696 B2 * | 8/2007 | Rabkin et al. | 623/1.11 |
| 7,285,130 B2 * | 10/2007 | Austin | 623/1.12 |
| 7,300,438 B2 * | 11/2007 | Falwell et al. | 606/41 |
| 7,331,958 B2 * | 2/2008 | Falwell et al. | 606/41 |
| 7,377,906 B2 * | 5/2008 | Selkee | 604/95.04 |
| 7,384,426 B2 * | 6/2008 | Wallace et al. | 623/1.12 |
| 7,506,650 B2 * | 3/2009 | Lowe et al. | 128/830 |
| 7,550,001 B2 * | 6/2009 | Dorn et al. | 623/1.12 |
| 7,591,268 B2 * | 9/2009 | Lowe et al. | 128/830 |
| 7,682,358 B2 * | 3/2010 | Gullickson et al. | 606/41 |
| 2001/0027323 A1 * | 10/2001 | Sullivan et al. | 606/108 |
| 2001/0037084 A1 * | 11/2001 | Nardeo | 604/95.04 |
| 2002/0072710 A1 * | 6/2002 | Stewart et al. | 604/164.02 |
| 2002/0077691 A1 * | 6/2002 | Nachtigall | 623/1.12 |
| 2002/0177766 A1 * | 11/2002 | Mogul | 600/374 |
| 2002/0177772 A1 * | 11/2002 | Altman et al. | 600/431 |
| 2003/0097128 A1 * | 5/2003 | Hayzelden | 606/41 |
| 2003/0145915 A1 | 8/2003 | Shimada | |
| 2004/0006380 A1 * | 1/2004 | Buck et al. | 623/1.11 |
| 2004/0059288 A1 * | 3/2004 | Webler et al. | 604/95.04 |
| 2004/0087971 A1 * | 5/2004 | Arnott | 606/127 |
| 2004/0092962 A1 * | 5/2004 | Thornton et al. | 606/139 |
| 2004/0127912 A1 | 7/2004 | Rabkin et al. | |
| 2004/0148009 A1 * | 7/2004 | Buzzard et al. | 623/1.12 |
| 2004/0181140 A1 * | 9/2004 | Falwell et al. | 600/374 |
| 2004/0181239 A1 * | 9/2004 | Dorn et al. | 606/108 |
| 2004/0193180 A1 * | 9/2004 | Buzzard et al. | 606/108 |
| 2004/0199236 A1 * | 10/2004 | Laske et al. | 607/129 |
| 2005/0021123 A1 * | 1/2005 | Dorn et al. | 623/1.11 |
| 2005/0070844 A1 * | 3/2005 | Chow et al. | 604/95.04 |
| 2005/0080476 A1 * | 4/2005 | Gunderson et al. | 623/1.11 |
| 2005/0222583 A1 * | 10/2005 | Cano et al. | 606/108 |
| 2005/0240254 A1 * | 10/2005 | Austin | 623/1.11 |
| 2005/0288551 A1 * | 12/2005 | Callister et al. | 600/115 |
| 2006/0173524 A1 * | 8/2006 | Salahieh et al. | 623/1.11 |
| 2007/0191925 A1 * | 8/2007 | Dorn | 623/1.12 |
| 2008/0243224 A1 * | 10/2008 | Wallace et al. | 623/1.11 |

FOREIGN PATENT DOCUMENTS

| | | |
|---|---|---|
| WO | WO98/23241 | 6/1998 |
| WO | WO 00/00104 | 1/2000 |
| WO | WO03/002019 | 1/2003 |
| WO | WO 3039345 A2 * | 5/2003 |
| WO | WO2004/096015 | 11/2004 |

* cited by examiner

STENT DELIVERY SYSTEM WITH MULTIPLE EVENLY SPACED PULLWIRES

TECHNICAL FIELD

This invention relates generally to biomedical systems for treating vascular conditions. More specifically, the invention relates to a stent delivery system having a catheter with two or more pullwires evenly spaced about the central axis of the catheter.

BACKGROUND OF THE INVENTION

Stents are cylindrical devices that are radially expandable to hold open a segment of a vessel or other anatomical lumen after deployment in the lumen. Various types of stents are in use, including balloon expandable and self-expanding stents. Balloon expandable stents generally are conveyed to the area to be treated on balloon catheters. A self-expanding stent is conveyed to a treatment site while compressed within a sheath. Once positioned, the sheath is retracted, allowing expansion of the stent.

The sheath may be retracted using a pullwire that extends from the proximal end of the stent delivery system (the end nearest the treating clinician) to the distal end of the system. In prior art systems in which the stent delivery system is guided to the desired treatment area over a guidewire, either the guidewire or the pullwire has been positioned off-center within a catheter. An off-center guidewire increases the difficulty of tracking a catheter over the guidewire. An off-center pullwire can cause a portion of the catheter to turn (to be pulled into a curved configuration) as the off-center pullwire is retracted, potentially displacing the catheter within a vessel.

Positioning multiple pullwires within a catheter such that the pullwires balance one another eliminates the problem of the catheter being pulled into a curved configuration. However, multiple pullwires held rigidly by a handle such as is typically used to retract a sheath can stiffen the catheter so that it is no longer adequately flexible to be delivered to many treatment sites.

Therefore, it would be desirable to have an improved stent delivery system that overcomes the aforementioned and other disadvantages

SUMMARY OF THE INVENTION

One aspect according to the present invention is a system for treating a vascular condition. The system comprises a catheter, a plurality of pullwires, and a pivoting connector. The catheter has a plurality of pullwire lumens evenly spaced about a central axis of the catheter. The pullwires are received within the pull wires lumens. The pivoting connector is operably attached to a proximal portion of each pullwire.

Another aspect according to the present invention is a stent delivery system. The system comprises a catheter, a stent, a retractable sheath, and a plurality of pullwires. The system may further comprise a pivoting connector. The catheter includes a plurality of pullwire lumens evenly spaced about the central axis of the catheter. The stent is mounted on a distal portion of the catheter. The retractable sheath encloses the stent. The pullwires are received within the pullwire lumens and are attached to the sheath. The pivoting connector is operably attached to proximal portions of the pullwires.

Another stent delivery system according to the present invention comprises an inner member, a stent, a catheter, and a plurality of pullwires. The system may further comprise a pivoting connector. The stent is mounted on the inner member. The catheter encloses at least a portion of the stent. The catheter includes a plurality of pullwire lumens evenly spaced about a central axis of the catheter. The pullwires are received within the pullwire lumens. The pivoting connector is operably attached to proximal portions of the pullwires.

The aforementioned and other features and advantages of the invention will become further apparent from the following detailed description, read in conjunction with the accompanying drawings, which are not to scale. The detailed description and drawings are merely illustrative of embodiments according to the invention rather than limiting.

BRIEF DESCRIPTION OF THE DRAWINGS

Like reference numbers are used throughout the drawings to refer to like elements.

DETAILED DESCRIPTION

One aspect according to the present invention is a system for treating a vascular condition. A portion of one embodiment of the system is illustrated at 100 in FIG. 1. The system comprises a catheter 110, two pullwires 120a and 120b, a pivoting pullwire connector 130, a master pullwire 140, and a guidewire 150. Catheter 110 includes two pullwire lumens 112a and 112b. Catheter 110 also includes a central guidewire lumen 114 within which guidewire 150 is received. Catheter 110 is shown in cross-section to reveal structures within. Only a proximal portion of system 100 is shown.

Figure 1:
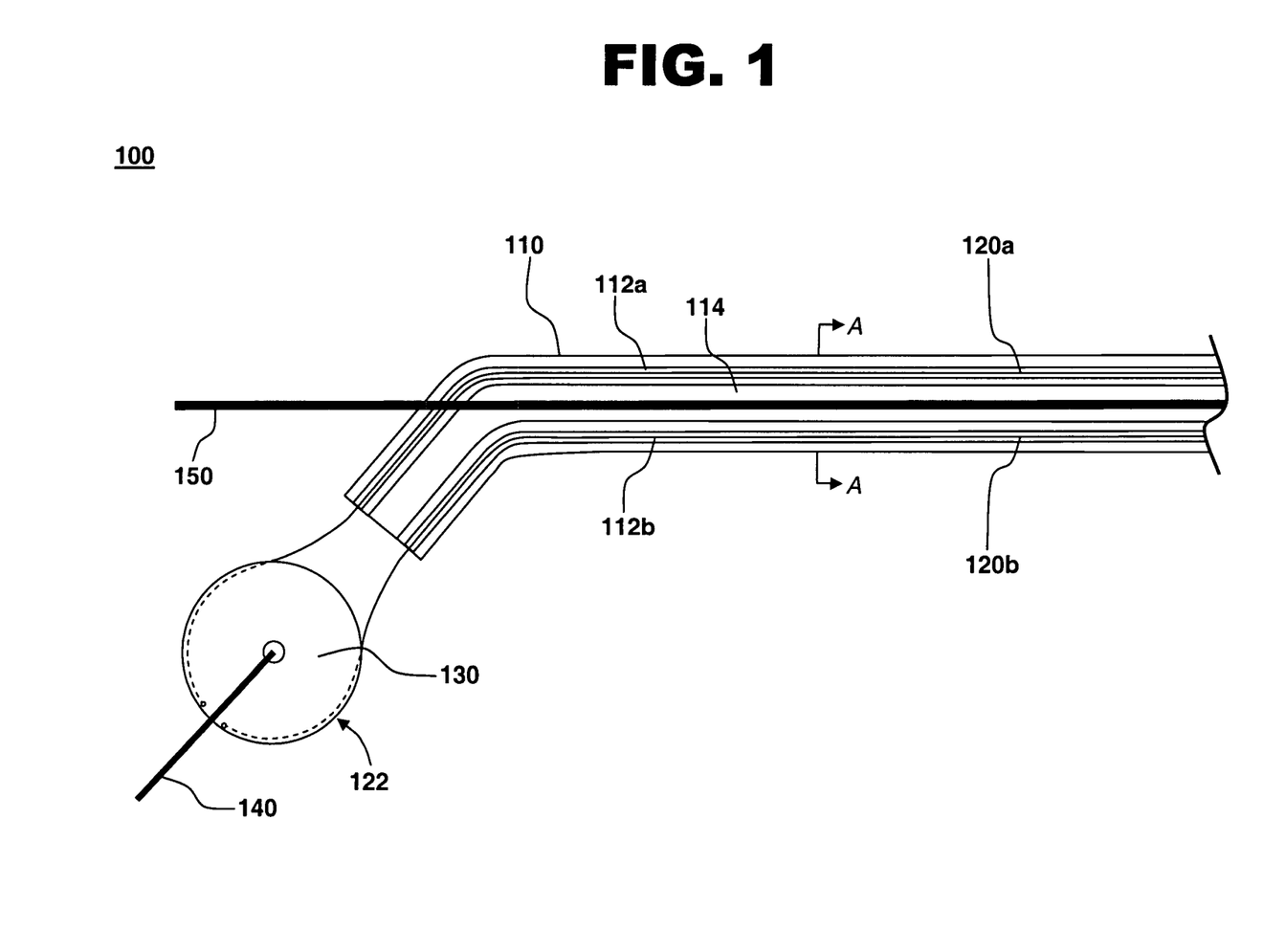
FIG. 1 is an illustration of a portion of one embodiment of a system for treating a vascular condition, in accordance with the present invention.
Figure 2:
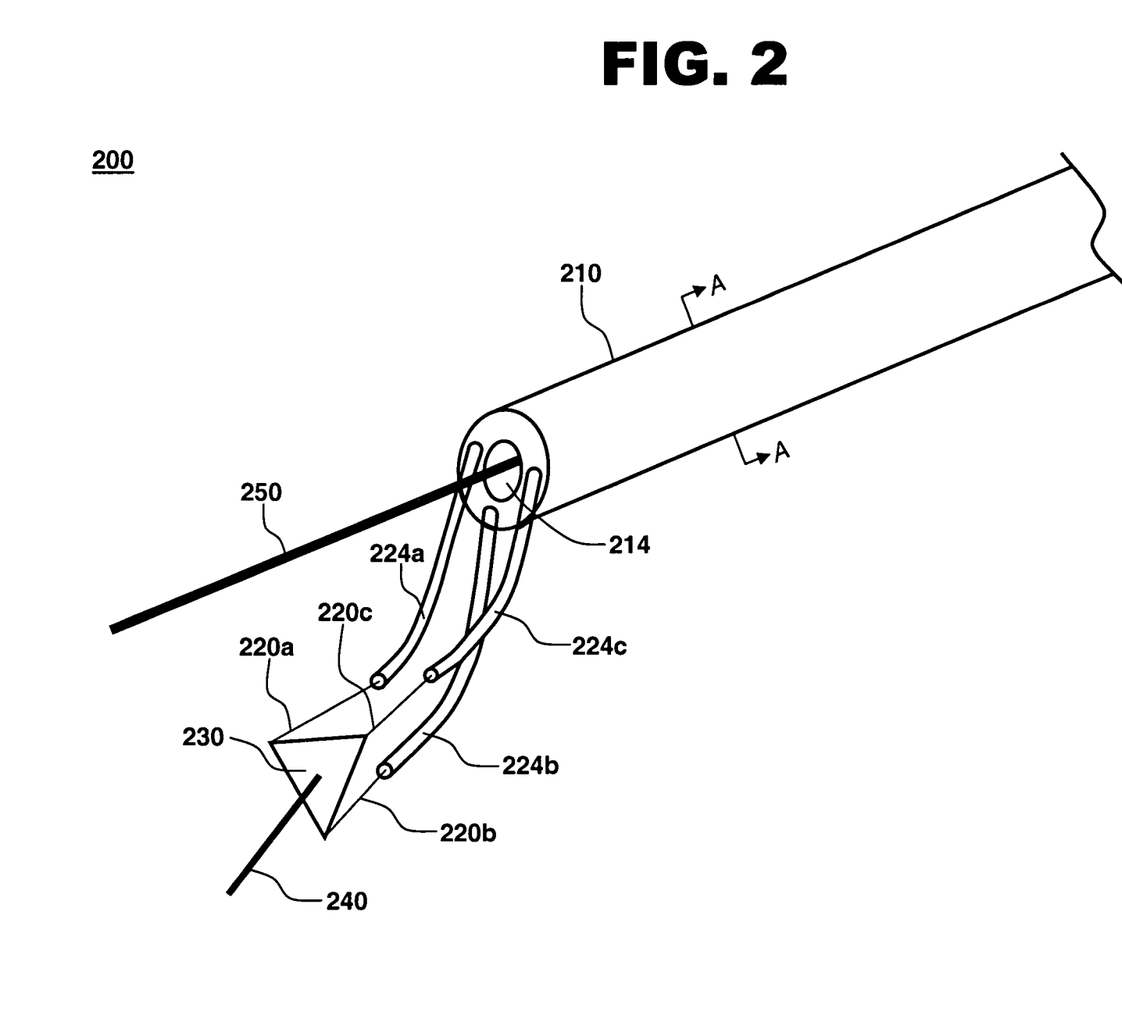
FIG. 2 is an illustration of another embodiment of a system for treating a vascular condition, in accordance with the present invention.
Figure 2A:
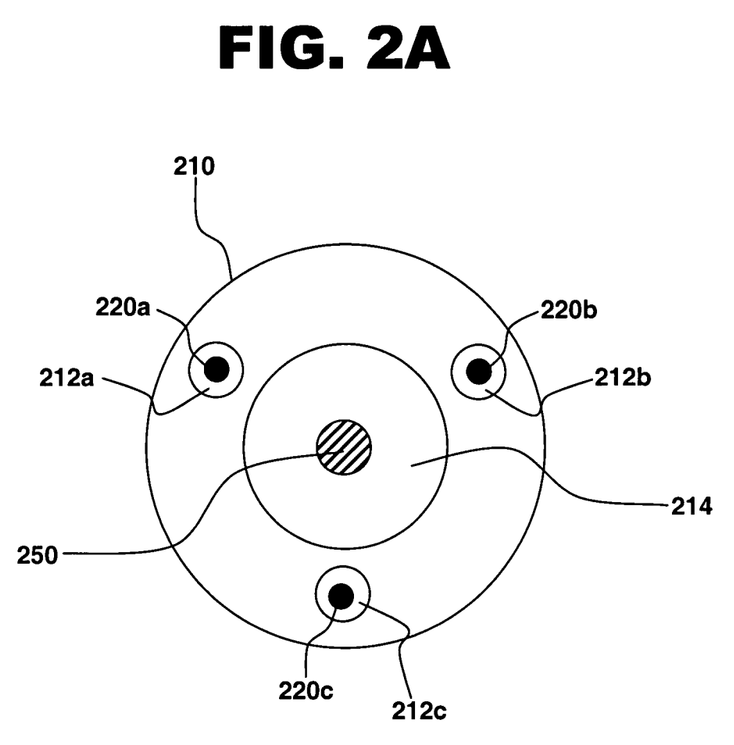
FIG. 2A is an enlarged cross-sectional view of a segment of the system of FIG. 2.

Catheter 110 is formed using one or more biocompatible materials such as polyurethane, polyethylene, nylon, or polytetrafluoroethylene (PTFE). In the present embodiment, catheter 110 includes two pullwire lumens 112a and 112b and a guidewire lumen 114. One skilled in the art will appreciate that a system in accordance with the present invention has at least two, but may have more than two, pullwire lumens. For example, FIGS. 2 and 2A illustrate a system having three pullwire lumens.

Figure 1A:
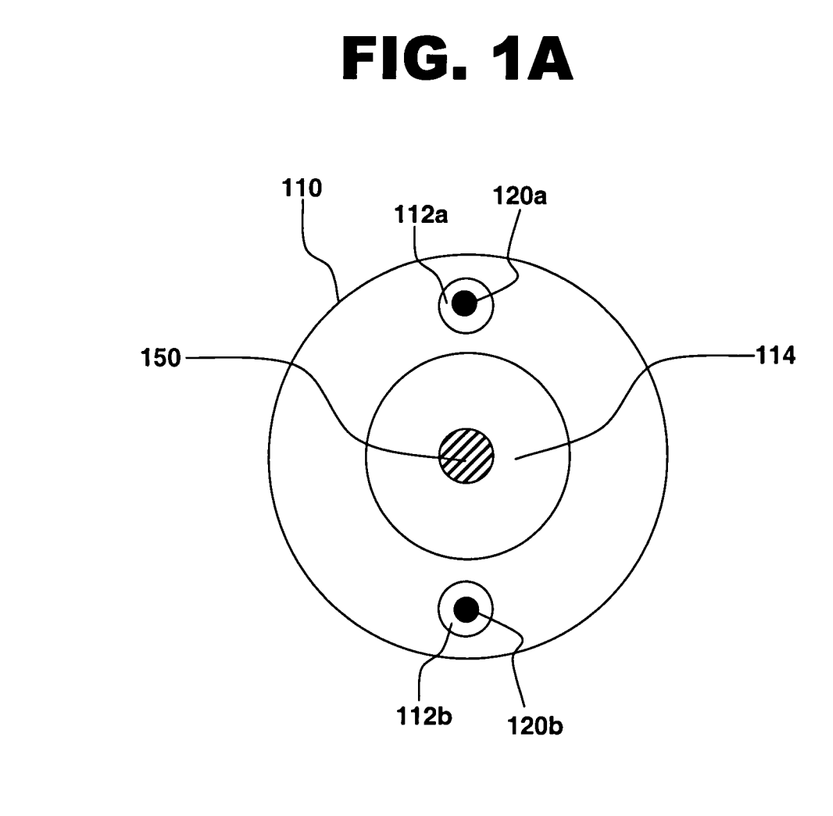
FIG. 1A is an enlarged cross-sectional view of a segment of the system of FIG. 1.

Pullwire lumens 112a,b are evenly spaced about the central axis of catheter 110. That is, the lumens are circumferentially equidistant one from another, and each lumen is positioned the same distance from the central axis of the catheter. This is best seen in FIG. 1A, which shows a cross-sectional view of catheter 110. Pullwire lumen 112a is shown at the top of the figure, with pullwire lumen 112b positioned directly opposite pullwire lumen 112a. Thus, the lumens are circumferentially equidistant from one another. Pullwire lumens 112a and 112b are also equidistant from guidewire 150, which is shown positioned at the central axis of catheter 110.

Pullwires 120a and 120b are received within pullwire lumens 112a and 112b, respectively. The pullwires may be either metallic or nonmetallic filaments or hypotubes. The pullwires may be formed using materials such as stainless steel, titanium, a nickel-titanium alloy, a nickel-cobalt alloy, another cobalt alloy, tantalum, polypropylene, polyethylene, polyurethane, polytetrafluoroethylene (PTFE), polyester (Dacron®), nylon, combinations thereof, and the like. One skilled in the art will appreciate that the number of pullwires may vary, with the number of pullwires typically being equal to the number of pullwire lumens. Where the number of pullwires is less than the number of pullwire lumens, the pullwires are positioned such that they are evenly spaced about the central axis of the catheter. For example, three pullwires may be positioned in a catheter having six pullwire lumens, with every other lumen containing a pullwire.

Pullwires 120a,b exit pullwire lumens 112a,b proximally via openings at the proximal ends of the pullwire lumens. As seen in FIG. 1, guidewire 150 exits catheter 110 through an opening or slit in the wall of the catheter. The proximal end of catheter 110 is bent, and the opening or slit is made in a portion of the catheter that falls between the two pullwires, thus allowing pullwires 120a,b and guidewire 150 to operate without interfering with one another.

Proximal portions of pullwires 120a,b are attached to connector 130. In the present embodiment, connector 130 is similar to a pulley wheel, having a groove 122 formed in at least a portion of the outer surface of the wheel. Other connectors are possible, including, but not limited to, those illustrated in FIGS. 2-4. Pullwires 120a,b are attached to connector 130 such that proximal portions of the pullwires (shown in phantom in FIG. 1) are received within, and are free to move within, groove 122. One skilled in the art will appreciate that separate grooves, one to accommodate each individual pullwire, may be used in place of the single groove. While not shown in FIG. 1, a person skilled in the art understands that the proximal end of the catheter would be connected in a common handle (pull member) to facilitate the application of the relative forces needed to pull the sheath (pullwire) while holding the center (middle) member stationary with respect to the sheath (pullwire) as the sheath and center member are moved relative to one another.

Master pullwire 140 is attached to the radial center point or hub of connector 130 in such a way that connector 130 is free to pivot about the attachment point. For example, master pullwire 140 may be rigid and rotatably attached to a face of connector 130 using attachment means known in the art such as a movable rivet passing through the connector. Alternatively, a flexible master pullwire 140 may be looped through a lumen or hole formed at the hub of connector 130 and doubled back on itself, leaving connector 130 free to rotate about the portion of master pullwire 140 received within the lumen or hole.

As connector 130 rotates in a clockwise direction (i.e., pivots to the right), pullwire 120a moves in a distal direction, while pullwire 120b moves in a proximal direction. Similarly, as connector 130 rotates in a counterclockwise direction (i.e., pivots to the left), pullwire 120a moves in a proximal direction, while pullwire 120b moves in a distal direction. Thus, the movement of connector 130 permits an effective lengthening of one pullwire and a corresponding shortening of the other pullwire, the difference in lengths being dependent upon the radius of connector 130. This action allows master pullwire 140 and pullwires 120a,b to remain substantially taut as system 100 is advanced to a treatment site, with the pivoting of connector 130 permitting pullwires 120a,b to move within pullwire lumens 112a,b as needed to accommodate flexure of catheter 110.

FIG. 2 illustrates another embodiment of a system for treating a vascular condition, according to the present invention. System 200 comprises a catheter 210; three pullwires 220a, 220b, and 220c; a pivoting pullwire connector 230; a master pullwire 240; and a guidewire 250. Catheter 210 includes three pullwire lumens 212a, 212b, and 212c. Catheter 210 also includes a central guidewire lumen 214 within which guidewire 250 is received. Only a proximal portion of system 200 is shown.

Pullwire lumens 212a,b,c are evenly spaced about the central axis of catheter 210. That is, consecutive pullwire lumens are circumferentially equidistant one from another and are equidistant from the central axis of the catheter. This is best seen in FIG. 2A, which shows an enlarged cross-sectional view of a segment of system 200.

In the embodiment seen in FIG. 2, guidewire 250 exits the proximal end of guidewire lumen 214, rather than through an opening in the wall of the catheter as in system 100. The portions of pullwires 220a,b,c extending proximally from catheter 210 are partially enclosed in flexible conduits 224a,b,c.

As seen in FIG. 2, each of three pullwires 220a,b,c is attached to a vertex of a substantially flat, triangular plate. The triangle forming connector 230 is preferably equilateral, with master pullwire 240 attached to the midpoint of the equilateral triangle.

A connector according to the present invention may assume various shapes, depending on the number of pullwires in the system and the desired range of motion (or "throw") of the connector. For example, two additional connector designs are shown in FIGS. 3 and 4.

Figure 3:
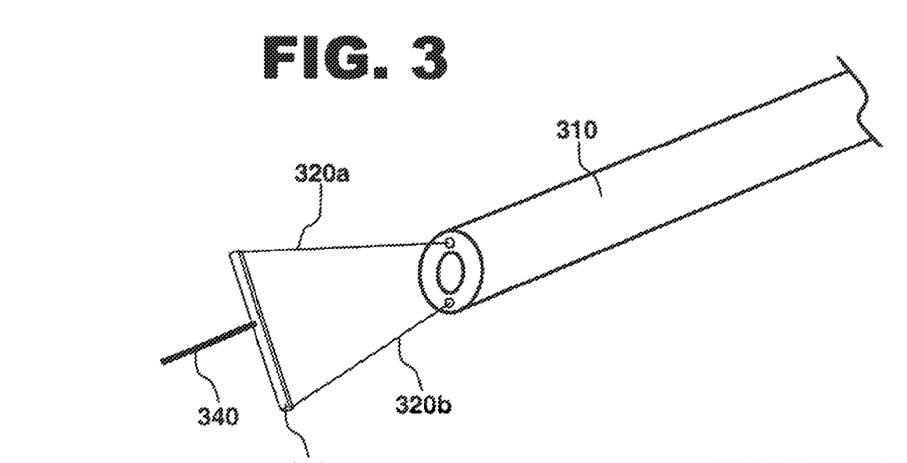
FIGS. 3 and 4 illustrate pull wire connectors.

As seen in FIG. 3, each of two pullwires 320a,b is attached to an end of a narrow, elongated bar- or rod-like connector 330. Master pullwire 340 is attached to the midpoint of connector 330. The length of connector 330 may be varied to provide the desired range of motion, with a longer connector providing greater range of motion.

Figure 4:
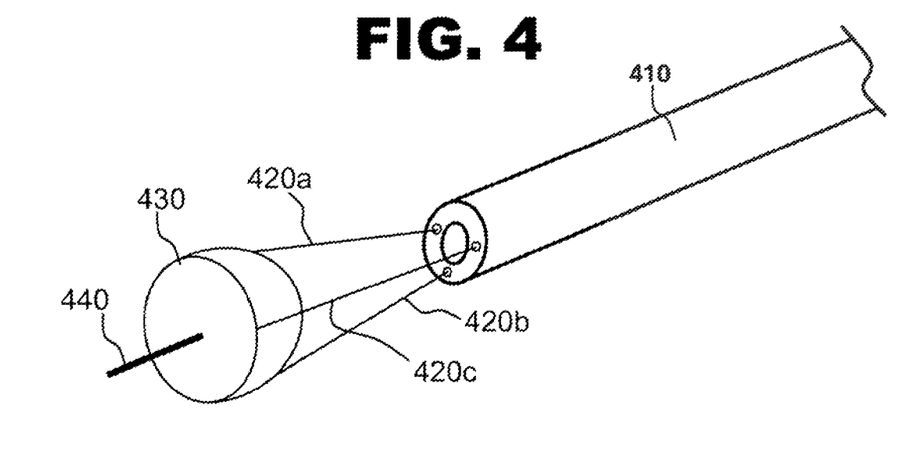

FIG. 4 shows a hemispheric connector 430 designed to accommodate three pullwires 420a,b,c, with master pullwire 440 attached to the midpoint of the flat surface of the hemisphere. In this design, the diameter of the sphere may be varied to provide greater or lesser range of motion.

A system such as has been described above may be used in deploying a self-expanding stent at a treatment site. For example, in one aspect, a self-expanding stent may be mounted on a catheter having multiple pullwire lumens, with the catheter acting as an inner member. In another aspect, the self-expanding stent may be constrained by the catheter, with the catheter acting as an outer sheath. As used herein, the term "stent" is intended to include not only stents, but also grafts, stent-grafts, and other self-expanding endoluminal prostheses.

Figure 5:
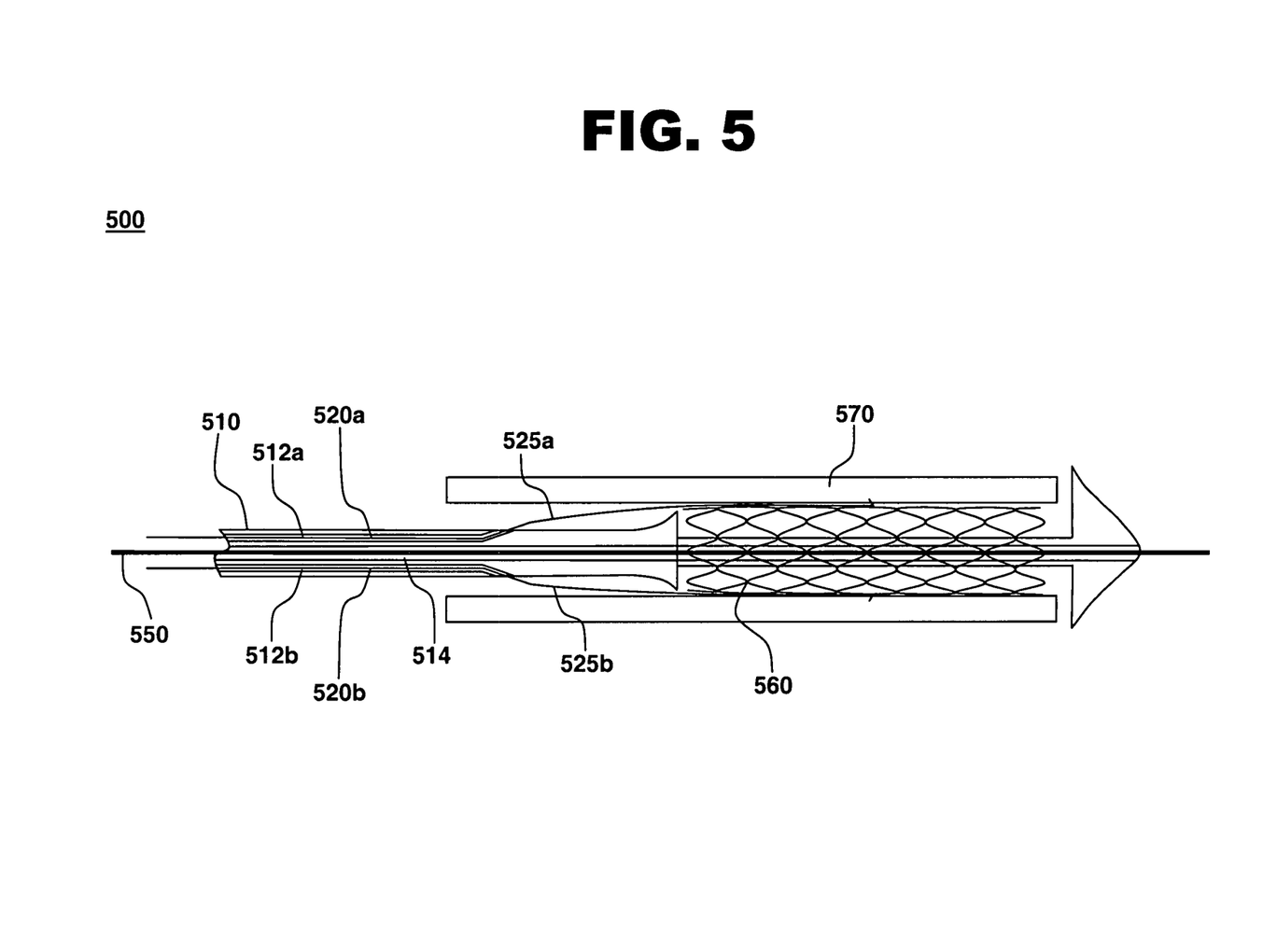
FIG. 5 is an illustration of one embodiment of a stent delivery system, in accordance with the present invention.

FIG. 5 illustrates one embodiment of a stent delivery system according to the present invention in which a catheter having multiple pullwire lumens serves as an inner member. System 500 comprises a catheter 510, two pullwires 520a and 520b, a guidewire 550, a stent 560, and a retractable sheath 570. Catheter 510 is shown in cross-section to reveal two pullwire lumens 512a and 512b and a guidewire lumen 514. FIG. 5 shows a distal portion of system 500. At its proximal end, system 500 includes a pivoting connector and a master pullwire such as are described above and illustrated in FIGS. 1 and 2-4.

Catheter 510 is formed using one or more biocompatible materials such as polyurethane, polyethylene, nylon, and polytetrafluoroethylene (PTFE). Pullwire lumens 512a,b are evenly spaced about the central axis of catheter 510. That is, the lumens are circumferentially equidistant one from another, and each lumen is positioned the same distance from the central axis of the catheter. One skilled in the art will appreciate that a catheter according to the present aspect of the invention may include more than two pullwire lumens. Where a catheter has three or more pullwire lumens, consecutive pullwire lumens are circumferentially equidistant one from another as well as being equidistant from the central axis of the catheter.

Pullwires 520a and 520b are received within pullwire lumens 512a and 512b, respectively. The pullwires may be either metallic or nonmetallic filaments or hypotubes. The pullwires may be formed using materials such as stainless steel, titanium, a nickel-titanium alloy, a nickel-cobalt alloy, another cobalt alloy, tantalum, polypropylene, polyethylene, polyurethane, polytetrafluoroethylene (PTFE), polyester (Dacron®), nylon, combinations thereof, and the like. One skilled in the art will appreciate that the number of pullwires may vary, with the number of pullwires typically being equal to the number of pullwire lumens. Where the number of pullwires is less than the number of pullwire lumens, the pullwires are positioned such that they are evenly spaced about the central axis of the catheter. For example, three pullwires may be positioned in a catheter having six pullwire lumens, with every other lumen receiving a pullwire.

As seen in FIG. 5, pullwires 520a,b exit pullwire lumens 512a,b distally via openings in the outer surface of catheter 510 that communicate with the pullwire lumens. Pullwire lumens 512a,b are shown extending through only a proximal portion of catheter 510 but may, in another embodiment, extend to the distal end of the catheter.

At its distal end, each pullwire 520a,b is attached to retractable sheath 570 by means of, for example, an adhesive bond or an attachment ring. Sheath 570 encloses stent 560, which is mounted on catheter 510 by being radially compressed or crimped about the catheter. Sheath 570 is at least as long as stent 560 and has an inner diameter large enough to receive compressed stent 560. Sheath 570 is formed using one or more biocompatible materials such as polyurethane, polytetrafluoroethylene (PTFE), or polyethylene.

Stent 560 is a self-expanding stent. Stent 560 is formed from, for example, a nickel-titanium alloy, a nickel-cobalt alloy, a cobalt alloy, a thermoset plastic, stainless steel, a stainless steel alloy, a biocompatible shape-memory material, a biocompatible superelastic material, combinations of the above, and the like. Prior to deployment, stent 560 presses against the inner diameter of sheath 570.

Pullwires 520a,b exit pullwire lumens 512a,b distally via openings in the outer surface of catheter 510 that communicate with the pullwire lumens. In the present embodiment, portions 525a,b of pullwires 520a,b extend distally across the outer surface of catheter 510 and underlie a proximal portion of sheath 570. The distal ends of pullwires 520a,b are attached to a mid-portion of sheath 570 at points located approximately midway along the length of stent 560. In order for sheath 570 to be fully retracted from stent 560 when pullwires 520a,b are retracted, pullwire distal portions 525a,b are at least as long as stent 560.

Attaching to a mid-portion of the sheath, rather than to the proximal end of the sheath, causes the portion of the sheath proximal to the pullwire attachment points to be either in compression when the pullwires are retracted to retract the sheath or, at a minimum, under less tension than would be the case if the pullwires were attached to the proximal end of the sheath. This aids in preventing deformation of the sheath, which can result in the sheath cinching down onto the stent as the sheath is retracted.

One skilled in the art will appreciate that other configurations of the pullwires and sheath are possible. These include, but are not limited to, the following examples. In one embodiment, rather than the pullwires underlying the sheath, the pullwires may be received within passages formed in the wall of the sheath that extend from the proximal end of the sheath to a mid-portion of the sheath, with the attachment point for each pullwire approximately midway along the length of stent. In this embodiment, the pullwires exit the catheter pullwire lumens proximal to the sheath and extend distally over the outer surface of the catheter.

Alternatively, each pullwire may exit its pullwire lumen through the distal end of an elongated slit in the outer surface of the catheter that communicates with the pullwire lumen. In this example, as the pullwires are retracted, the distal ends of the pullwires move proximally through the slits, allowing the sheath to be fully retracted from the stent.

In another embodiment, the pullwires may be attached to a proximal end of the sheath and extend distally over the outer surface of the catheter, with the exposed portions of the pullwires being at least as long as the stent. Alternatively, the pullwires may be attached to a proximal end of the sheath and extend from an elongated slit as described above.

In the present embodiment, system 500 includes a pivoting connector and a master pullwire such as are described above and illustrated in FIGS. 1 and 2-4, with proximal portions of pullwires 520a,b attached to the connector. Sheath 570 may be retracted by drawing on the master pullwire, which retracts pullwires 520a and 520b.

The range of motion of the pivoting connector allows the pullwires to assume different lengths. Thus, a pullwire positioned over the outer curve of a flexed catheter may be longer than a pullwire positioned within the inner curve of the catheter, preventing the catheter from being deformed or displaced by the action of retracting pullwires 520a,b to retract sheath 570. Retracting sheath 570 allows stent 560 to self-expand radially outward from catheter 510, thereby deploying the stent.

The range of motion of the pivoting connector also allows the master pullwire and pullwires 520a,b to remain substantially taut as system 500 is advanced to a treatment site, with the pivoting of the connector permitting pullwires 520a,b to move within pullwire lumens 512a,b as needed to accommodate flexure of catheter 510.

Figure 6:
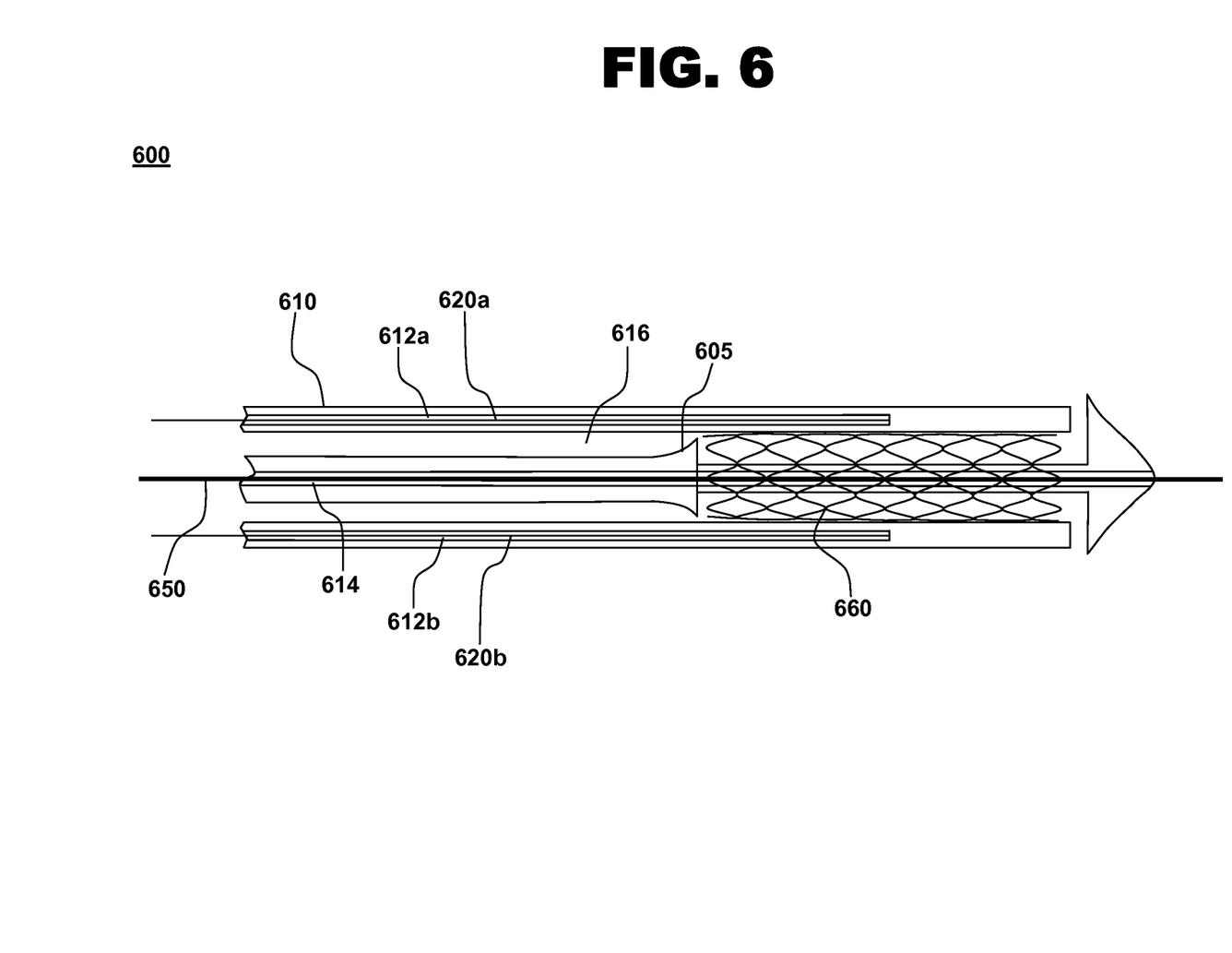
FIG. 6 is an illustration of another embodiment of a stent delivery system, in accordance with the present invention.

FIG. 6 illustrates an embodiment of a stent delivery system according to the present invention in which a catheter having multiple pullwire lumens serves as an outer sheath. System 600 comprises an inner member 605, a catheter 610, two pullwires 620a and 620b, a guidewire 650, and a stent 660. Inner member 605, shown in cross-section, includes a guidewire lumen 614. Catheter 610 is also shown in cross-section to reveal two pullwire lumens 612a and 612b and a central lumen 616. FIG. 6 shows a distal portion of system 600. At its proximal end, system 600 includes a pivoting connector and a master pullwire such as are described above and illustrated in FIGS. 1 and 2-4.

Inner member 605 is an elongated structure that, in the present embodiment, includes a central lumen 614 within which guidewire 650 is received. Inner member 605 is formed using one or more biocompatible materials including, but not limited to, polyurethane, polytetrafluoroethylene (PTFE), polyethylene, nylon, nitinol, or stainless steel.

Stent 660 is mounted on a distal portion of inner member 605 by radially compressing the stent about the inner member. In the present embodiment, stent 660 is a self-expanding stent formed from, for example, a nickel-titanium alloy, a nickel-cobalt alloy, a cobalt alloy, a thermoset plastic, stainless steel, a stainless steel alloy, a biocompatible shape-memory material, a biocompatible superelastic material, combinations of the above, and the like.

Inner member 605 is received within catheter 610. Prior to deployment, stent 660 is enclosed by and presses against the inner diameter of catheter 610. Catheter 610 is formed using one or more biocompatible materials such as polyurethane, polyethylene, nylon, or polytetrafluoroethylene (PTFE). Catheter 610 includes pullwire lumens 612a and 612b evenly spaced about the central axis of catheter 610. That is, the lumens are circumferentially equidistant one from another, and each lumen is positioned the same distance from the central axis of the catheter. Pullwire lumens 612a,b are shown extending through only a proximal portion of catheter 610 but may, in another embodiment, extend from the proximal end to the distal end of the catheter.

A catheter according to the present aspect of the invention may include more than two pullwire lumens. Where a catheter has three or more pullwire lumens, consecutive pullwire lumens are circumferentially equidistant one from another as well as being equidistant from the central axis of the catheter.

Pullwires 620a and 620b are received within pullwire lumens 612a and 612b, respectively. The pullwires may be either metallic or nonmetallic filaments or hypotubes. The pullwires may be formed using materials such as stainless steel, titanium, a nickel-titanium alloy, a nickel-cobalt alloy, another cobalt alloy, tantalum, polypropylene, polyethylene, polyurethane, polytetrafluoroethylene (PTFE), polyester (Dacron®), nylon, combinations thereof, and the like. The number of pullwires in system 600 may vary, with the number of pullwires typically being equal to the number of pullwire lumens.

As seen in FIG. 6, the distal ends of pullwires 620a,b are attached to catheter 610 at points located approximately midway along the length of stent 660. One skilled in the art will appreciate that the pullwires may be attached anywhere along the length of catheter 610, with the attachment points chosen to limit deformation of the catheter as the sheath is retracted. For example, where a particularly long stent or a stent having substantial expansive strength is to be delivered using system 600, the attachment points may be located adjacent to the distal end of catheter 610, placing the portion of the catheter proximal to the attachment points in compression or reduced tension and assuring that catheter 610 does not deform and cinch down onto the stent.

In the present embodiment, system 600 includes a pivoting connector and a master pullwire such as are described above and illustrated in FIGS. 1 and 2-4, with proximal portions of pullwires 620a,b attached to the connector. Catheter 610 may be retracted by drawing on the master pullwire, which retracts pullwires 620a and 620b. Retracting catheter 610 allows stent 660 to self-expand radially outward from inner member 605, thereby deploying the stent.

The range of motion of the pivoting connector allows the pullwires to assume different lengths. Thus, a pullwire positioned over the outer curve of a flexed catheter may be longer than a pullwire positioned within the inner curve of the catheter, preventing the catheter from being deformed or displaced by the action of retracting pullwires 620a,b to retract catheter 610.

The range of motion of the pivoting connector also allows the master pullwire and pullwires 620a,b to remain substantially taut as system 600 is advanced to a treatment site, with the pivoting of the connector permitting pullwires 620a,b to move within pullwire lumens 612a,b as needed to accommodate flexure of catheter 610.

Figure 7A:
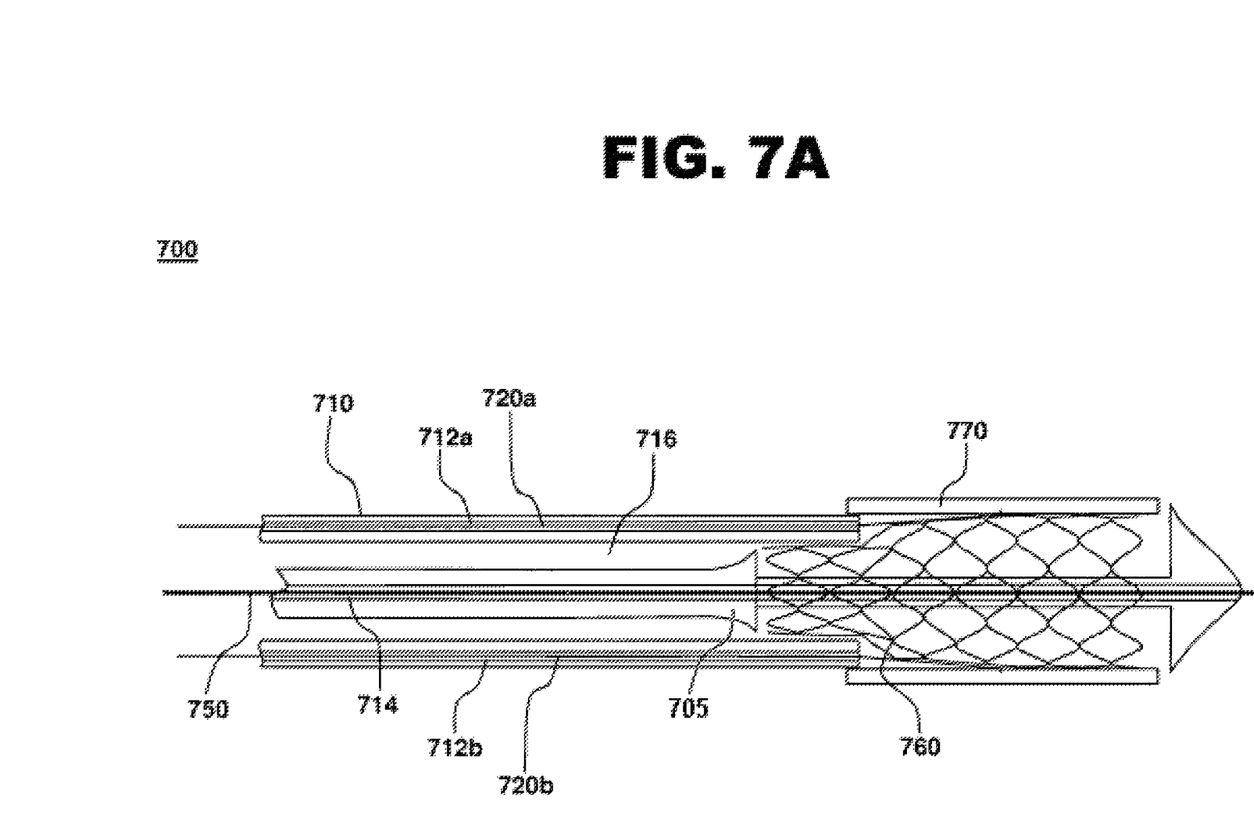
FIGS. 7A and 7B show the system of FIG. 7 at two stages of deployment of a stent.
Figure 7B:
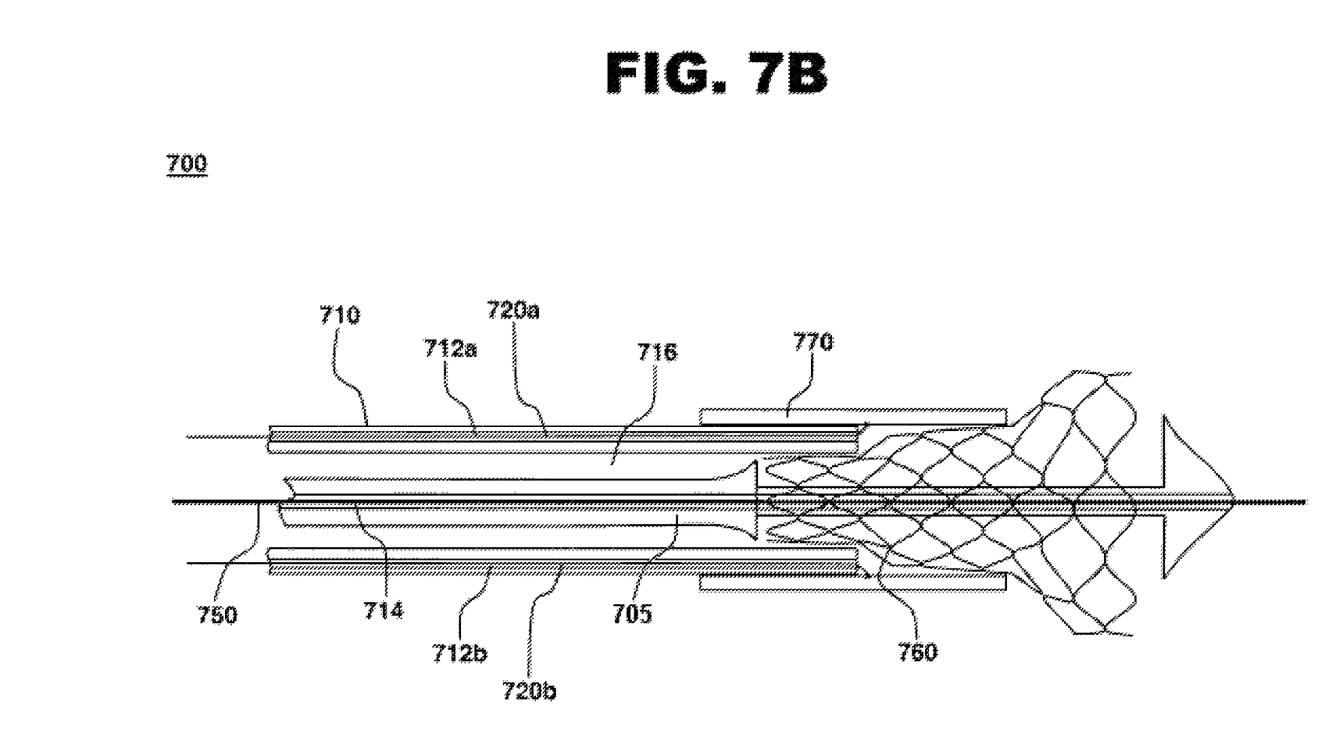
Figure 7C:
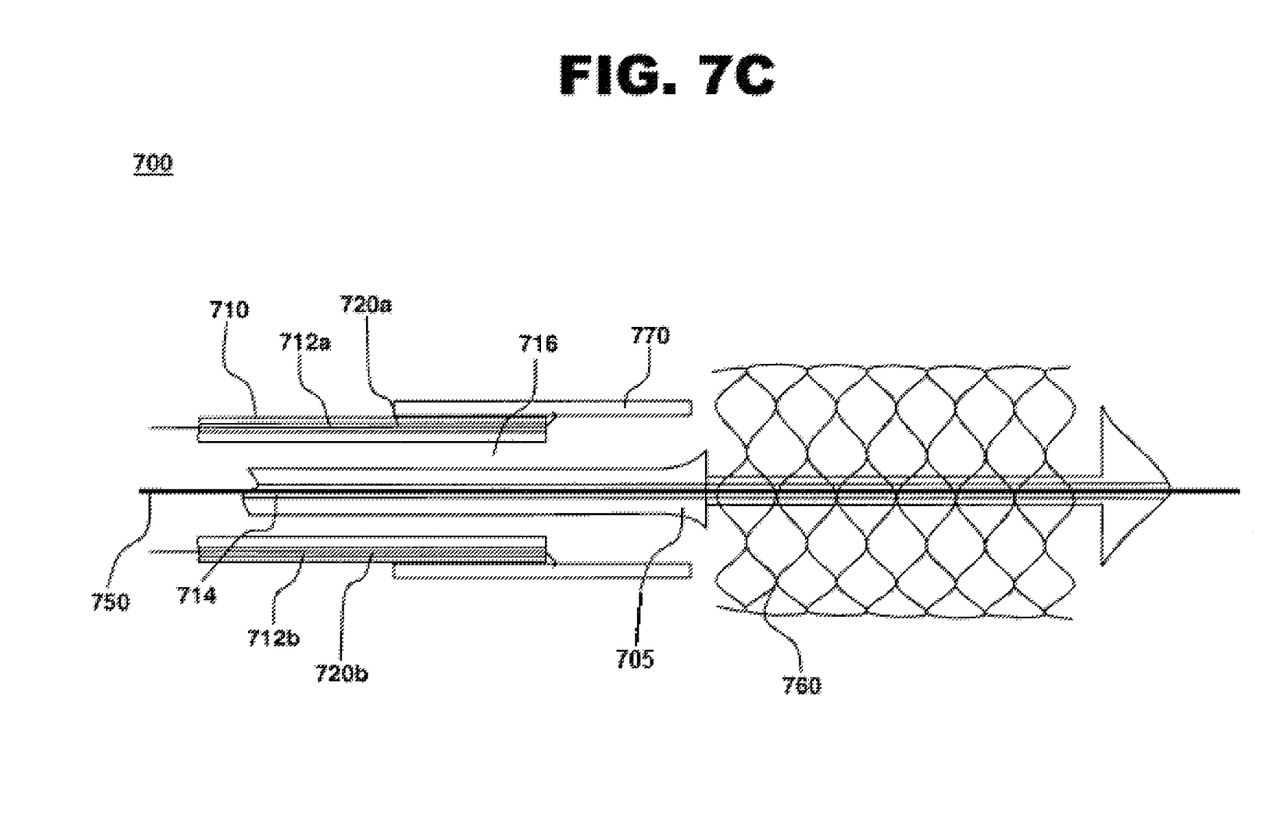
FIG. 7 is an illustration of still another embodiment of a stent delivery system, in accordance with the present invention.

FIGS. 7A-7C illustrate another embodiment of a stent delivery system according to the present invention in which a catheter having multiple pullwire lumens serves as an outer sheath. System 700 is similar to system 600 in materials and design, comprising an inner member 705, a catheter 710, two pullwires 720a and 720b, a guidewire 750, and a stent 760. In addition, system 700 comprises a distal sheath 770. Inner member 705, catheter 710, and distal sheath 770 are shown in cross-section to reveal structures within. FIGS. 7A-7C show a distal portion of system 700. At its proximal end, system 700 includes a pivoting connector and a master pullwire such as are described above and illustrated in FIGS. 1 and 2-4.

Inner member 705 includes central lumen 714, within which guidewire 750 is received. Inner member 705 is received within catheter 710.

Catheter 710 includes two pullwire lumens 712a,b evenly spaced about the central axis of catheter 710. That is, the lumens are circumferentially equidistant one from another, and each lumen is positioned the same distance from the central axis of the catheter. A catheter according to the present aspect of the invention may include more than two pullwire lumens. Where a catheter has three or more pullwire lumens, consecutive pullwire lumens are circumferentially equidistant one from another as well as being equidistant from the central axis of the catheter. Catheter 710 also includes a central lumen 716.

Pullwire lumens 712a,b extend the entire length of catheter 710 and have outlets at both the proximal and distal ends of the catheter. Pullwires 720a and 720b are received within pullwire lumens 712a and 712b, respectively, with portions of the pullwires extending from both the distal and the proximal ends of the pullwire lumens.

The distal ends of pullwires 720a,b are attached to distal sheath 770 by, for example, adhesive bonding. In the present embodiment, pullwires 720a,b underlie a proximal portion of distal sheath 770 and are attached to distal sheath 770 approximately midway along the length of the distal sheath.

Self-expanding stent 760 is mounted on a distal portion of inner member 705. Catheter 710 encloses only a proximal portion of stent 760, thus acting as a proximal sheath. A distal portion of stent 760 extends from the distal end of catheter 710 and is enclosed by distal sheath 770. Thus, prior to deployment, the proximal portion of stent 760 presses against the inner diameter of catheter 710, while the distal portion presses against the inner diameter of distal sheath 770.

As can be seen in FIG. 7A, the inner diameter of distal sheath 770 is larger than the outer diameter of catheter 710, allowing the proximal end of distal sheath 770 to enclose the distal end of catheter 710 during delivery of stent 760 to a treatment site, and also allowing distal sheath 770 to be retracted over the outer surface of catheter 710 for deployment of stent 760.

In the present embodiment, system 700 includes a pivoting connector and a master pullwire such as are described above and illustrated in FIGS. 1 and 2-4, with proximal portions of pullwires 720a,b attached to the pivoting connector. Pullwires 720a,b are retracted by drawing on the master pullwire. The range of motion of the pivoting connector allows the pullwires to assume different lengths. Thus, a pullwire positioned over the outer curve of a flexed catheter may be longer than a pullwire positioned within the inner curve of the catheter, preventing the catheter from being deformed or displaced by the action of retracting pullwires 720*a,b*. In addition, the range of motion allows the master pullwire and pullwires 720*a,b* to remain substantially taut as system 700 is advanced to a treatment site, with the pivoting of the connector permitting pullwires 720*a,b* to move within pullwire lumens 712*a,b* as needed to accommodate flexure of catheter 710.

FIGS. 7B and 7C illustrate system 700 at two stages of deployment of stent 760. FIG. 7B shows distal sheath 770 retracted to initiate deployment of stent 760, with a distal portion of stent 760 shown released and expanded. Distal sheath 770 is retracted by drawing on the master pullwire, which retracts pullwires 720*a* and 720*b*. Note that catheter 710 is held stationary as distal sheath 770 is retracted.

In FIG. 7C, both distal sheath 770 and catheter 710 are shown retracted, with stent 760 fully deployed. Catheter 710 may be retracted by pulling on pullwires 720*a,b* or by pulling on the distal end of catheter 710 itself.

System 700 provides improved stent placement accuracy over prior art systems for at least two reasons. First, because distal sheath 770 encloses only a distal portion of stent 760, the area of contact between the sheath and the stent is minimized, thereby minimizing the friction that must be overcome to withdraw distal sheath 770 and reducing the risk that stent 760 may be longitudinally compressed or displaced during retraction of distal sheath 770. Second, because catheter 710 is held stationary until after stent 760 is partially deployed and thereby anchored in the vessel, retracting catheter 710 to fully deploy stent 760 is unlikely to either damage or dislodge the stent.

Figure 8:
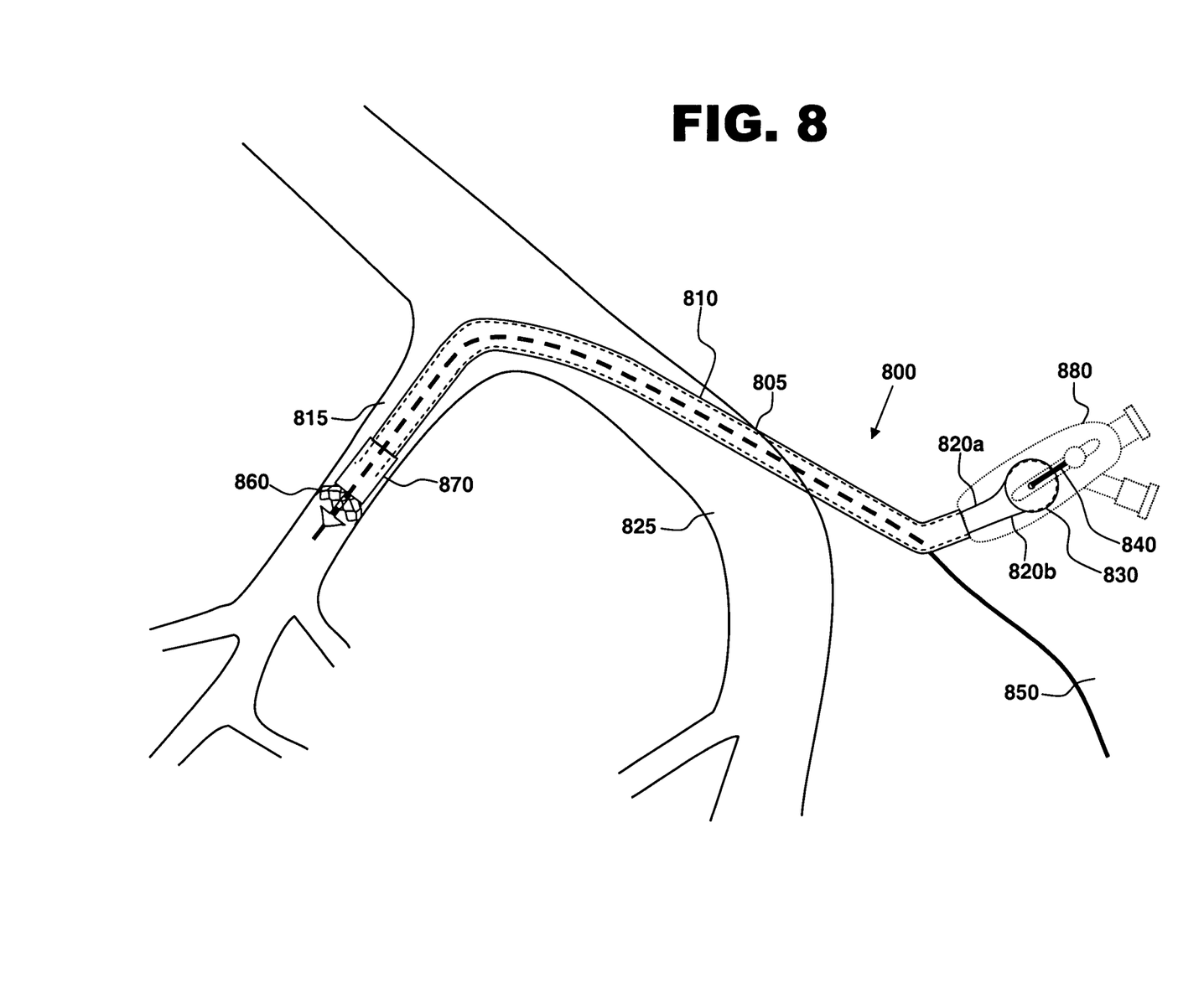
FIG. 8 is an illustration of a stent delivery system in accordance with the present invention being introduced into an internal iliac artery.

FIG. 8 illustrates a stent delivery system according to the present invention being introduced via a percutaneous access site 805 into an internal iliac artery 815. System 800 includes a proximal portion such as is seen in FIG. 1 and a distal portion such as is seen in FIG. 7B. One skilled in the art will appreciate that any of the proximal portions illustrated in FIG. 14 may be combined with any of the distal portions illustrated in FIGS. 1-7A,B,C.

As seen in FIG. 8, system 800 becomes flexed as it passes from femoral artery 825 into internal iliac artery 815. Pullwire 820*a* is positioned over the outer curve of flexed catheter 810, while pullwire 820*b* is positioned within the inner curve of flexed catheter 810. Both pullwires are shown in phantom within catheter 810, extending from pivoting connector 830, at the proximal end of system 800, to sheath 870, at the distal end of system 800. The system has been delivered over guidewire 850, which exits catheter 810 through an opening or slit in the wall of the catheter.

Sheath 870 is shown partially retracted, with a distal portion of stent 760 shown released and expanded. Sheath 870 has been drawn proximally by drawing on master pullwire 840, which is attached via pivoting connector 830 to pullwires 820*a* and 820*b*, which are attached to sheath 870. An apparatus for drawing on master pullwire 840 and enclosing pivoting connector 830 is shown in phantom at 880 in FIG. 8. The apparatus shown is intended to be just one example of an apparatus that may be used with any of the embodiments illustrated and described above.

The range of motion of pivoting connector 830 allows pullwires 820*a* and 820*b* to assume different lengths. As seen in FIG. 8, pivoting connector 830 has rotated in a counterclockwise direction to allow pullwire 820*a*, positioned over the outer curve of flexed catheter 810, to be longer than pullwire 820*b*. Because pullwires 820*a* and 820*b* are able to move independently of one another, catheter 810 maintains full flexibility while being delivered to a treatment site and is not deformed or displaced by the action of retracting pullwires 820*a* and 820*b* to retract sheath 870.

It will be obvious to one skilled in the art that, while discussed above in the context of delivering a self-expanding stent, a catheter having two or more pullwires evenly spaced about the central axis of the catheter may be used for a variety of purposes. As just one example, a treatment device such as biopsy forceps may be mounted on a distal portion of the catheter, with the pullwires used to activate the device. Thus, although various embodiments of the invention are disclosed herein, changes and modifications can be made without departing from the spirit and scope of the invention.

What is claimed is:

1. A catheter system for treating a vascular condition with a stent, comprising:
   a catheter shaft defining a central lumen and a plurality of pullwire lumens evenly spaced about a central axis of the catheter shaft;
   an inner member disposed in the central lumen, the inner member being operable to receive the stent thereon;
   a catheter sheath slideably disposed about the catheter shaft and operable to enclose at least a portion of the stent;
   a plurality of pullwires received within the pullwire lumens and thereby being evenly spaced about the central axis of the catheter shaft, the plurality of pullwires being coupled to the catheter sheath to slide the catheter sheath axially relative to the catheter shaft;
   a pivoting connector having an end, wherein proximal portions of said plurality of pullwires are operably attached to and evenly distributed about an end of the pivoting connector; and
   a master pull wire connected to the midpoint of said pivoting connector, wherein said master pull wire is operably connected to facilitate retraction of said catheter sheath by retracting said midpoint of said pivoting connector to cause a relative catheter sheath retraction motion between said inner member and said pivoting connector.

2. The system of claim 1 wherein the pivoting connector is a wheel having at least one groove formed in an outer surface of the wheel.

3. The system of claim 1 wherein the pivoting connector is a narrow, elongated member.

4. The system of claim 1 wherein the pivoting connector is a substantially flat, triangular plate.

5. The system of claim 1 wherein the pivoting connector is a hemisphere.

6. The system of claim 1 wherein the inner member includes a central guidewire lumen.

7. The system of claim 6 further comprising:
   a guidewire.

8. The system of claim 1 further comprising:
   a flexible conduit enclosing a proximal portion of each pullwire.

9. The system of claim 1 wherein a distal end of each of the plurality of pullwires is coupled to the catheter sheath at a location approximately midway along a length of the stent or distal to the location approximately midway along the length of the stent.

10. A stent delivery system, comprising:
    a catheter shaft having a plurality of pullwire lumens evenly spaced about a central axis of the catheter;
    a stent mounted on a distal portion of the catheter shaft;
    a retractable sheath enclosing the stent and slideably disposed about the catheter shaft; and a plurality of pullwires received within the pullwire lumens, the plurality of pullwires attached to the retractable sheath to slide the retractable sheath axially relative to the catheter shaft, a pivoting connector having an end, wherein proximal portions of the plurality of pullwires are operably attached to and evenly spaced about an end of the pivoting connector, and a master pullwire operably attached to the midpoint of said pivoting connector which retracts said pivoting connector to cause retraction of said retractable sheath.

11. The system of claim 10 wherein the pullwires are attached to a mid-portion of the retractable sheath.

12. The system of claim 10 wherein the catheter shaft includes a central guidewire lumen.

13. The system of claim 12 further comprising:
a guidewire.

14. The system of claim 10 wherein a distal end of each of the plurality of pullwires is coupled to the sheath at a location approximately midway along a length of the stent or distal to the location approximately midway along the length of the stent.

15. A stent delivery system, comprising:
an inner member having an axial length;
a stent mounted on the inner member;
a catheter and sheath assembly enclosing at least a portion of the stent, the catheter and sheath assembly having an integrated catheter shaft and sheath, the catheter shaft slideably disposed about the inner member and including a plurality of pullwire lumens evenly spaced about a central axis of the catheter shaft; and a plurality of pullwires having proximal and distal portions received within the pullwire lumens;

wherein the distal portions of said plurality of pullwires are coupled to the sheath to slide the sheath axially relative to the inner member, wherein proximal portions of said plurality of pullwires are operably attached to and evenly distributed about an end of a pivoting connector, wherein a master pullwire is operably attached to a midpoint of said pivoting connector to retract said pivoting connector to retract said pullwires to retract said catheter and sheath assembly.

16. The system of claim 15 wherein the inner member includes a central guidewire lumen.

17. The system of claim 16 further comprising:
a guidewire.

18. The system of claim 16 wherein a distal end of each of the plurality of pullwires is coupled to the sheath at a location approximately midway along a length of the stent or distal to the location approximately midway along the length of the stent.

* * * * *